US012023182B2

(12) United States Patent
Demers et al.

(10) Patent No.: US 12,023,182 B2
(45) Date of Patent: *Jul. 2, 2024

(54) SYSTEM, METHOD, AND APPARATUS FOR REMOTE PATIENT CARE

(71) Applicant: DEKA Products Limited Partnership, Manchester, NH (US)

(72) Inventors: Jason A. Demers, Manchester, NH (US); Frederick Morgan, Bedford, NH (US); George W. Marchant, Jr., Goffstown, NH (US); David E. Collins, Amesbury, MA (US); Katie A. DeLaurentis, Northbrook, IL (US); Dean Kamen, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/411,574

(22) Filed: Aug. 25, 2021

(65) Prior Publication Data
US 2021/0378777 A1    Dec. 9, 2021

Related U.S. Application Data

(63) Continuation of application No. 16/683,637, filed on Nov. 14, 2019, now Pat. No. 11,109,934, which is a
(Continued)

(51) Int. Cl.
*A61B 50/31*    (2016.01)
*A61B 5/15*    (2006.01)
(Continued)

(52) U.S. Cl.
CPC ........ *A61B 50/31* (2016.02); *A61B 5/150022* (2013.01); *A61B 5/150305* (2013.01);
(Continued)

(58) Field of Classification Search
None
See application file for complete search history.

(56) References Cited

U.S. PATENT DOCUMENTS 5,801,755 A    9/1998    Echerer
5,848,700 A *  12/1998   Horn ...................... A61F 17/00
                                                        206/572
(Continued)

FOREIGN PATENT DOCUMENTS

WO    WO2016/090315 A1    6/2016

OTHER PUBLICATIONS

Adler, Ari T., "A Cost-Effective Portable Telemedicine Kit for Use in Developing Countries"; Thesis; Brandeis University, 1996; May 19, 2000; © 2000 Massachusetts Institute of Technology; pp. 1-96.
(Continued)

*Primary Examiner* — Farley Abad
*Assistant Examiner* — Dayton Lewis-Taylor
(74) *Attorney, Agent, or Firm* — Ira Stickler

(57) ABSTRACT

A portable patient-care kit is disclosed. The kit includes a housing, a plurality of compartments and a touch-screen user interface device. The housing forms a container space. The plurality of compartments is disposed within the container space such that each compartment is configured to retain at least one medical apparatus. The touch-screen user interface device has a transceiver that can communicate via a mobile data network.

17 Claims, 8 Drawing Sheets

Related U.S. Application Data continuation of application No. 15/163,906, filed on May 25, 2016, now Pat. No. 10,478,261.

(60) Provisional application No. 62/168,343, filed on May 29, 2015.

(51) Int. Cl.

| | |
|---|---|
| *A61B 10/00* | (2006.01) |
| *A61B 34/00* | (2016.01) |
| *A61B 90/30* | (2016.01) |
| *A61B 90/98* | (2016.01) |
| *A61M 16/00* | (2006.01) |
| *A61M 16/10* | (2006.01) |
| *B65D 5/00* | (2006.01) |
| *G16H 20/00* | (2018.01) |
| *G16H 40/67* | (2018.01) |
| *G16H 80/00* | (2018.01) |
| *A61B 5/157* | (2006.01) |
| *A61B 17/00* | (2006.01) |
| *A61B 50/00* | (2016.01) |
| *A61B 50/30* | (2016.01) |
| *G16H 10/65* | (2018.01) |
| *G16H 40/60* | (2018.01) |
| *G16H 40/63* | (2018.01) |

(52) U.S. Cl.
CPC ............ *A61B 10/007* (2013.01); *A61B 34/25* (2016.02); *A61B 90/30* (2016.02); *A61B 90/98* (2016.02); *A61M 16/0051* (2013.01); *A61M 16/021* (2017.08); *A61M 16/10* (2013.01); *B65D 5/0085* (2013.01); *G16H 20/00* (2018.01); *G16H 40/67* (2018.01); *G16H 80/00* (2018.01); *A61B 5/150343* (2013.01); *A61B 5/157* (2013.01); *A61B 2017/00199* (2013.01); *A61B 2017/00221* (2013.01); *A61B 2017/00734* (2013.01); *A61B 2050/0056* (2016.02); *A61B 2050/3008* (2016.02); *A61B 2050/311* (2016.02); *A61B 2560/0252* (2013.01); *A61B 2560/0257* (2013.01); *A61B 2562/029* (2013.01); *A61B 2562/182* (2013.01); *A61M 2202/0208* (2013.01); *A61M 2205/15* (2013.01); *A61M 2205/18* (2013.01); *A61M 2205/3569* (2013.01); *A61M 2205/3592* (2013.01); *A61M 2205/581* (2013.01); *A61M 2205/583* (2013.01); *A61M 2205/6054* (2013.01); *A61M 2209/06* (2013.01); *A61M 2209/084* (2013.01); *A61M 2230/04* (2013.01); *A61M 2230/205* (2013.01); *A61M 2230/30* (2013.01); *A61M 2230/50* (2013.01); *G16H 10/65* (2018.01); *G16H 40/60* (2018.01); *G16H 40/63* (2018.01)

(56) References Cited

U.S. PATENT DOCUMENTS

| | | | |
|---|---|---|---|
| 8,016,089 | B1 | 9/2011 | McNichols |
| 8,434,577 | B1 | 5/2013 | Al-Qaffas |
| 9,106,421 | B1 | 8/2015 | Singh et al. |
| D758,399 | S | 6/2016 | Kendler et al. |
| D760,288 | S | 6/2016 | Kendler et al. |
| D760,289 | S | 6/2016 | Kendler et al. |
| 9,364,394 | B2 | 6/2016 | Demers et al. |
| 9,372,486 | B2 | 6/2016 | Peret et al. |
| D760,782 | S | 7/2016 | Kendler et al. |
| D760,888 | S | 7/2016 | Gill et al. |
| 9,400,873 | B2 | 7/2016 | Kamen et al. |
| D767,756 | S | 9/2016 | Sabin |
| 9,435,455 | B2 | 9/2016 | Peret et al. |
| D768,716 | S | 10/2016 | Kendler et al. |
| 9,465,919 | B2 | 10/2016 | Kamen et al. |
| 9,488,200 | B2 | 11/2016 | Kamen et al. |
| 2002/0001794 | A1 | 1/2002 | Melker et al. |
| 2003/0058097 | A1* | 3/2003 | Saltzstein ............... G08B 1/08 340/815.4 |
| 2006/0006999 | A1* | 1/2006 | Walczyk ............... G06Q 10/08 340/572.1 |
| 2006/0259187 | A1* | 11/2006 | Berg ...................... G07F 9/026 221/9 |
| 2007/0095914 | A1 | 5/2007 | Noguchi |
| 2007/0135965 | A1 | 6/2007 | Nguyen et al. |
| 2007/0272746 | A1 | 11/2007 | Ortiz et al. |
| 2009/0108011 | A1 | 4/2009 | Heffron |
| 2010/0235782 | A1 | 9/2010 | Powell et al. |
| 2011/0102146 | A1 | 5/2011 | Giron |
| 2011/0130636 | A1* | 6/2011 | Daniel .................. B64C 39/024 709/201 |
| 2011/0197887 | A1 | 8/2011 | Truschel et al. |
| 2012/0095779 | A1 | 4/2012 | Wengrovitz et al. |
| 2012/0197090 | A1 | 8/2012 | Chen et al. |
| 2013/0023741 | A1 | 1/2013 | Ayanruoh |
| 2013/0043826 | A1 | 2/2013 | Workman et al. |
| 2013/0152175 | A1 | 6/2013 | Hromoko et al. |
| 2013/0176115 | A1 | 7/2013 | Puleston et al. |
| 2014/0064164 | A1 | 3/2014 | Nagaraj et al. |
| 2014/0128757 | A1 | 5/2014 | Banet et al. |
| 2014/0246991 | A1 | 9/2014 | Kim |
| 2014/0330428 | A1 | 11/2014 | Wolfe et al. |
| 2014/0379848 | A1 | 12/2014 | Sabbouh |
| 2015/0002606 | A1* | 1/2015 | Hyde ....................... H04N 7/14 348/14.02 |
| 2015/0137997 | A1 | 5/2015 | Huang |
| 2015/0151051 | A1 | 6/2015 | Tsoukalis |
| 2015/0192993 | A1 | 7/2015 | Pellaton |
| 2015/0237217 | A1 | 8/2015 | Roark et al. |
| 2015/0238228 | A1 | 8/2015 | Langenfeld et al. |
| 2016/0131272 | A1 | 5/2016 | Yoo et al. |
| 2016/0158437 | A1 | 6/2016 | Biasi et al. |
| 2016/0179086 | A1 | 6/2016 | Peret et al. |
| 2016/0184510 | A1 | 6/2016 | Kamen et al. |
| 2016/0203292 | A1 | 7/2016 | Kamen et al. |
| 2016/0262977 | A1 | 9/2016 | Demers et al. |
| 2016/0319850 | A1 | 11/2016 | Kamen et al. |
| 2016/0328900 | A1 | 11/2016 | Yong et al. |

OTHER PUBLICATIONS

AMD Global Telemedicine; "A Collaborative Patient Assessment Tool for Telemedicine Clinical Exams"; AGNES Interactive®; www.amdtelemedicine.com; info@amdtelemedicine.com; 321 Billerica Road, Chelmsford, MA 01824; Rev. Jan. 28, 2016; pp. 1-2.

AMD Global Telemedicine; Portable TeleClinic™ "Clinical Telemedicine in a Mobile Case"; http://www.amdtelemedicine.com/telemedicine-equipment/portable-teleclinic.html; May 26, 2016; pp. 1-2.

Becky; Albert Schweitzer Hospital; "VSee Telemedicine Kit Brings Harvard Doctors to Gabon Villagers"; Posted Jul. 18/ By becky (https://vsee.com/blog/author/becky/) / In Telemedicine News (https://vsee.com/blog/category/telemedicine-news/), VSee (https://vsee.co/blog/category/vsee/); https://vsee.com/blog/vsee-telemedicine-kit-in-africa/; May 26, 2016; pp. 1-14.

DIGIGONE Remote Communication Solutions; "Knock Big Data down to size""Remote Camera Kit"; sales@digigone.com; http://www.digigone.com/remote_cam_kit.php; May 26, 2016; p. 1.

VSee Telemedicine; "Simple, Secure Telemedicine Solutions"; VSee Telemedicine Kit—In Gabon and Beyond; https://vsee.com/telemedicine; May 26, 2016; © 2016 VSee; pp. 1-11.

VSee Video Telemedicine; VSee Product Catalog Web; © 2015VSee p. 1.

U.S. Appl. No. 62/168,343, filed May 29, 2015.

U.S. Appl. No. 15/163,906, filed May 25, 2016, US20160346056A1.

(56) References Cited

OTHER PUBLICATIONS

U.S. Appl. No. 16/683,637, filed Nov. 14, 2019, US20200078127A1.
U.S. Appl. No. 15/163,906, filed May 25, 2016.

* cited by examiner

SYSTEM, METHOD, AND APPARATUS FOR REMOTE PATIENT CARE

CROSS REFERENCE TO RELATED APPLICATIONS

The present application is a continuation application of U.S. patent application Ser. No. 16/683,637, filed Nov. 14, 2019 and entitled System, Method, and Apparatus for Remote Patient Care, which will be U.S. Pat. No. 11,109, 934, issuing on Sep. 7, 2021 which is a continuation application of U.S. patent application Ser. No. 15/163,906, filed May 25, 2016 and entitled System, Method, and Apparatus for Remote Patient Care, now U.S. Pat. No. 10,478,261 issued Nov. 19, 2019 which claims the benefit of U.S. Provisional Patent Application Ser. No. 62/168,343, filed May 29, 2015 and entitled System, Method, and Apparatus for Remote Patient Care which is hereby incorporated herein by reference in its entirety.

BACKGROUND

Relevant Field

The present disclosure relates to patient care. More particularly, the present disclosure relates to a system, method and apparatus for using a kit for providing patient care.

Description of Related Art

Healthcare may be delivered in a centralized, decentralized or hybride mode of care. For example, healthcare may be performed by a centralized institution or by smaller, localized care (e.g., in-home care). As care networks look to improve the value of every dollar spent they are learning that alternate care models, and hence environments, have the potential to both decrease expenditures and increase results. One of the key ingredients in this future ecosystem is the interplay between home care and retail medicine.

Some patients may be admitted to a healthcare institution that could potentially receive the same, or better, care at home using a leaner, more agile care model. To facilitate this type of care, patients will need access to the appropriate medical supplies and monitoring the patient would typically receive in a hospital bed with the aid of professional caregivers. Further, the professional caregiver will need an easy and predictable way to transform the patients residence into a recovery area outfitted with the appropriate technology to meet both the patient and the caregiver's needs.

SUMMARY

In accordance with one aspect of the present disclosure, a portable patient-care kit is provided. The kit includes two-housing portions, a plurality of compartments, a touch-screen user interface device, and a light bar. The two-housing portions pivotally coupled together to form a container space. The plurality of compartments is disposed within at least one of the housing portions such that each compartment is configured to retain at least one medical apparatus. The touch-screen user interface device has a transceiver that can communicate via a mobile data network. The light bar is disposed along an exterior of one of the two-housing portions configured provide light. The claims describe exemplary aspects and embodiments.

BRIEF DESCRIPTION OF THE DRAWINGS

These and other aspects will become more apparent from the following detailed description of the various embodiments of the present disclosure with reference to the drawings wherein.

DETAILED DESCRIPTION

Figure 1:
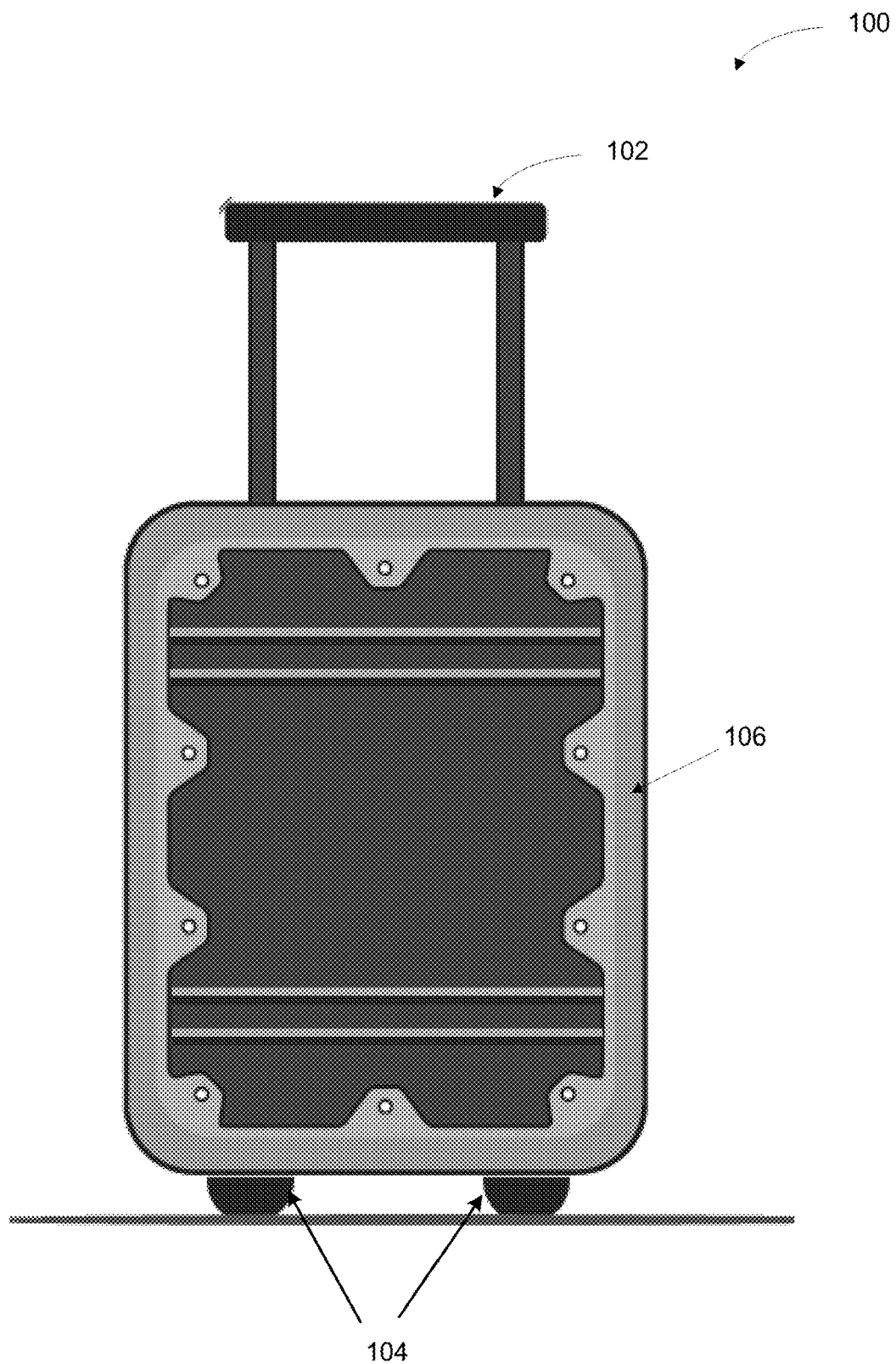
FIG. 1 shows a portable kit for patient care in a transportation configuration in accordance with an embodiment of the present disclosure.

FIG. 1 shows a portable kit 100 for patient care in transportation configuration in accordance with an embodiment of the present disclosure. The kit includes wheels 104 and a handle 102 to facilitate portability.

Figure 2:
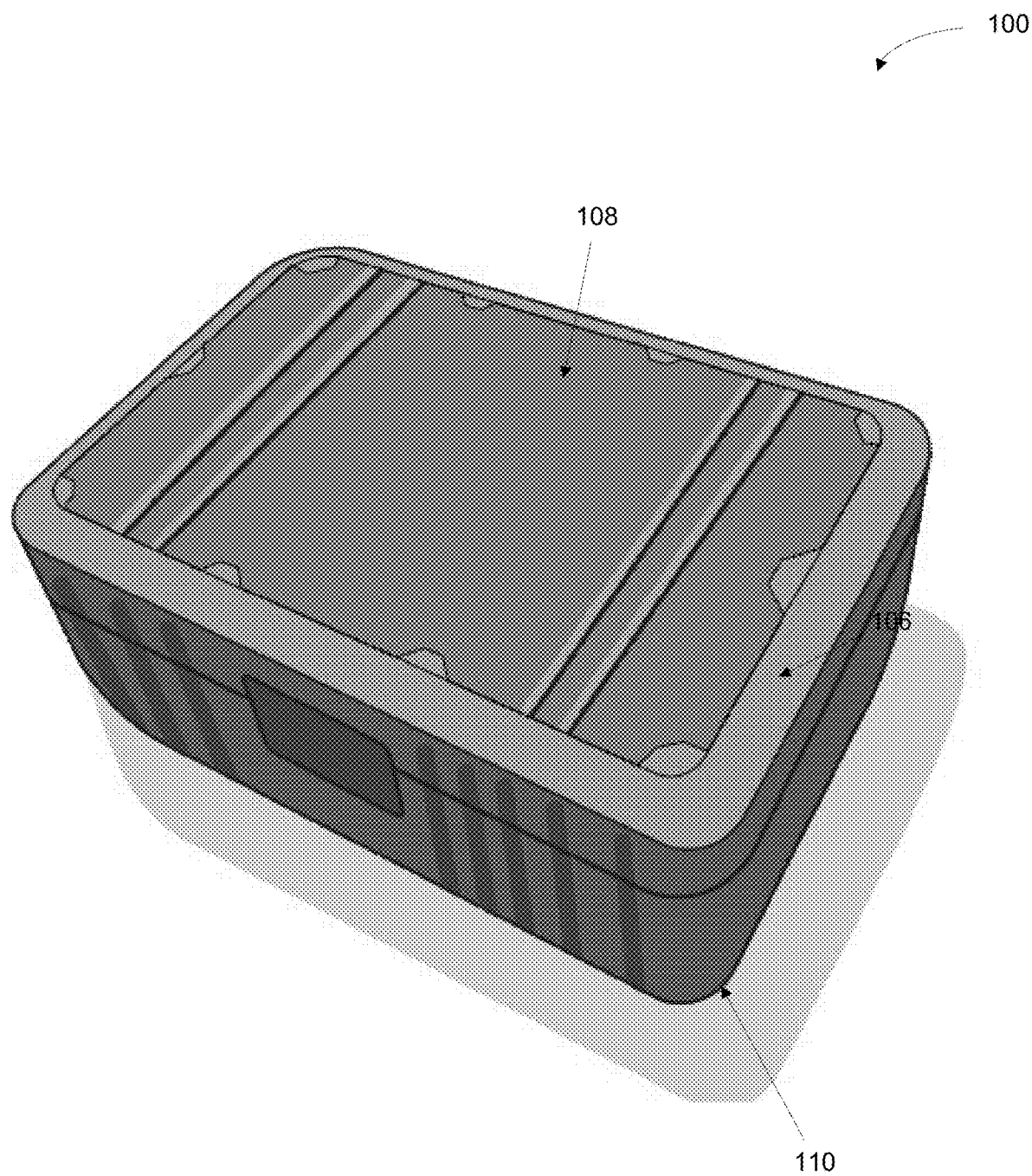
FIG. 2 shows the portable kit to illustrate the light bar that indicates a communicable status of the portable kit in accordance with an embodiment of the present disclosure.

FIG. 2 shows the portable kit to illustrate the light bar 106 that indicates a communicable status of the portable kit 100 in accordance with an embodiment of the present disclosure. A light bar 106 surrounds a portion of the kit. The light bar 106 may be formed by one or more LEDs having various colors or intensities with a light diffuser to give the appearance of a solidly lit bar 106. The light bar 106 may be illuminated with a variety of colors and intensities. The light bar 106 may also be illuminated with repeating or periodic patterns of color and/or intensities. For example, the light bar 106 may blink. In some embodiments of the present disclosure, one or more foldable legs may be pivotally connected to the kit 100 such that it may be stood on its side to form a table-like structure.

Figure 3:
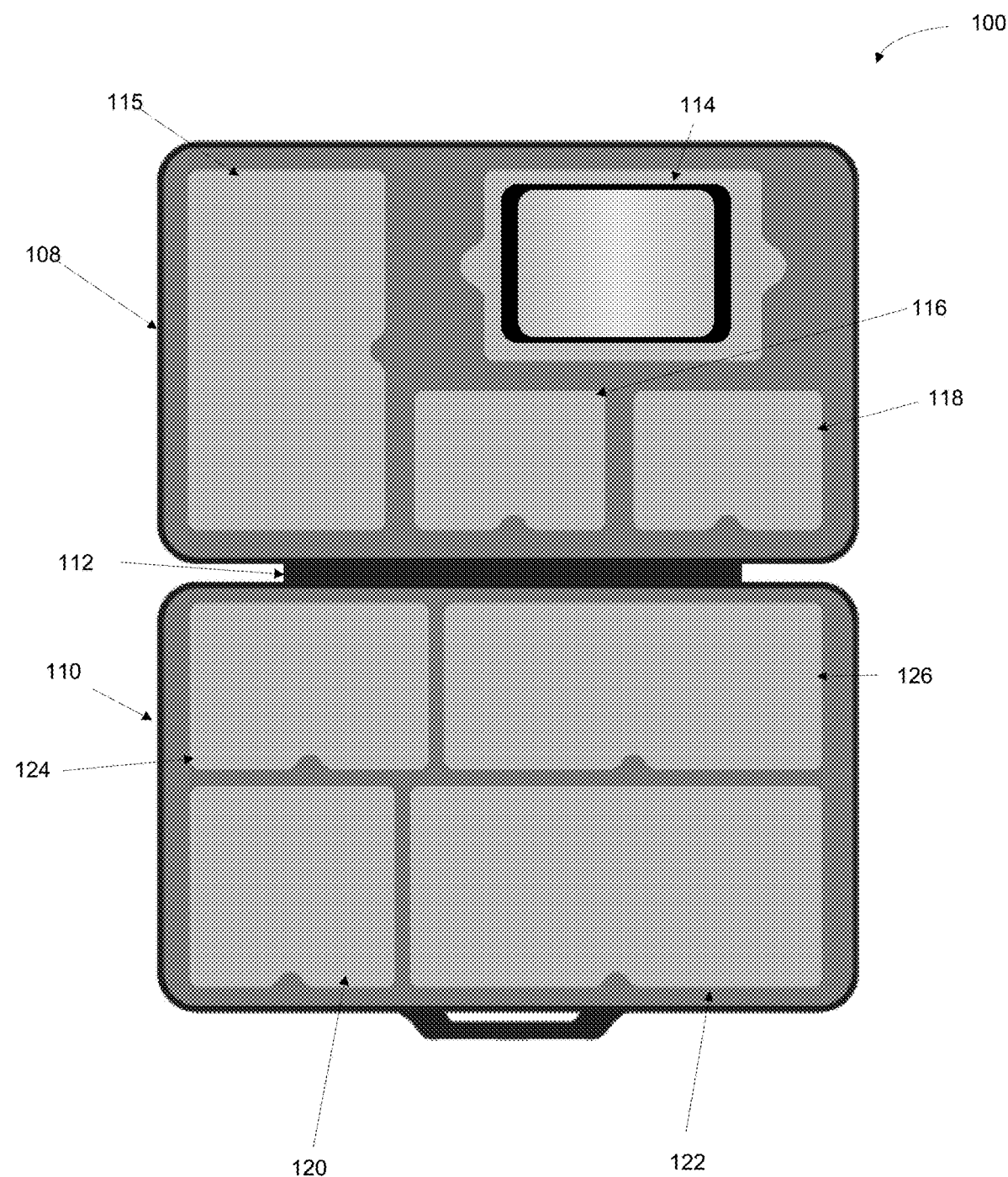
FIG. 3 shows an open portable kit to show the various compartments and a user interface in accordance with an embodiment of the present disclosure.

FIG. 3 shows an open portable kit 100 to show the various compartments and a user interface in accordance with an embodiment of the present disclosure. The kit 100 may be a "Universal" home kit. The "Universal" home kit may be a pre-packaged home care ecosystem that can be sent home with a patient as a result of a medical appointment and/or a caregiver-order prescription. For example, the kit 100 may be provided by a prescribing physician, institutional hospital, or retail healthcare clinic. The kit 100 may contain a set of integrated and easy to use medical equipment (i.e., medical apparatuses) appropriate for use in the home setting by a patient, family members and/or a licensed home caregiver.

The kit 100 may contain an integrated array of what is typically standalone equipment. The kit 100 may be sized to be about the size of a mid-sized travel suitcase as is typically used in air travel as a carry-on. The kit 100 has handles 102 and wheels 104 for ease of transport home by the patient (refer again to FIG. 1). As shown in FIG. 3, the kit 100 includes various compartments 115, 116, 118, 120, 122, 124, 126. The kit 100 also includes a user interface 114, e.g., a tablet. The kit 100 may include housing portions 108, 110 that are pivotable along a pivot (e.g., hinge) 112.

The kit includes a tablet 114 that may be a central control unit or may have a separate central control unit embedded within a housing portion 108, 110. The central control unit may incorporate a user interface, likely a touch screen graphical user interface, a cellular modem or other connectivity platform, Blue-tooth or other technology short-range interface radio(s). All of the medical apparatus found in the kit 100 may be pre-paired to the central control unit (e.g., tablet 114). Various medical apparatuses may be included within the kit 100, including, but not limited to, a weight scale, a pulse oximeter, a blood pressure meter, a thermometer, a blood glucose meter, a bioimpedance meter, and/or a spirometer. The tablet 114 may be pre-paired to all of the apparatuses over Bluetooth (e.g., Bluetooth LE).

The central control unit may provide a means for the kit to stream time-sequence data from the home directly into the electronic medical record. In some embodiments, the tablet 114 user interface provides "how-to" video support on demand, prompts users to perform care activities (such as changing dressings and taking medications), and serves as a channel for two-way communication between the patient and the licensed caregiver (telemedicine).

The medical apparatuses in the kit 100 may be an integrated platform. The kit 100 may limit the number of user interfaces the patient must learn by tight integration. By integrating the home care environment in the kit 100, the patient, in some embodiments, only needs to know how to use the tablet 114 and follow instructions provided on the tablet's 114 user interface based on the scenario at hand (e.g. taking a blood sugar reading when it is required).

The doors on the compartments various compartments 115, 116, 118, 120, 122, 124, 126 may open automatically. The doors may be transparent such that internal illumination can indicate to a user which compartment of the compartments various compartments 115, 116, 118, 120, 122, 124, 126 to open. In some embodiments, the doors of the compartments various compartments 115, 116, 118, 120, 122, 124, 126 are side illuminated.

In some embodiments, a power supply within the kit can power the medical apparatuses. The power supply may be connected to an AC outlet to provide inductive energy to the medical apparatus therein (or may power the devices directly through a wired connection). The power supply may include or be connected to a battery.

The tablet 114 or a central control unit may communicate data to a cloud server, which is accessible by a hospital, patient, and/or physician to retrieve data from a medical apparatus of any part of the kit 100.

In some embodiments, the kit includes an internal communications component, which may be an access point or hotspot for the tablet 114 and/or the medical apparatuses. The tablet 114 may be an access point or hotspot for the medical apparatuses and/or the communications components. The communication component and/or tablet 114 may include a secure link (e.g., encrypted and/or HIPPA compliant link) and/or an unsecured link.

In some embodiments, an environmental monitor component is disposed within the kit 100, which can monitor least one of temperature, humidity, location, vibration, shocks, and atmospheric pressure and communicate the measured parameter(s) to a cloud sever.

In some embodiments, an RFID reader is disposed within the kit 100. The RFID reader may communicate with the tablet 114 and/or the internal communications component. The RFID may be used to read RFID tags on the medical devices for inventory control purposes and/or to read RFID sensor values. An antenna may be in each compartment 115, 116, 118, 120, 122, 124, 126 such that the RFID reader can determine which of the compartments 115, 116, 118, 120, 122, 124, 126 the tag is located within. The RFID reader may determine when supplies are low and communicate that data to the tablet 114 (or internal communications device) which then orders new supplies.

In some embodiments, access control of the kit 100 may be implemented, including fingerprint, password, voice, or other access control. In yet additional embodiments, an audible and/or visual alarm system may be included within the kit 100 which can alarm if an external signal from the cloud is received, an excessive number of failed access attempts have been initiated, and/or the tablet 114 determines that the alarm should be sounded (e.g., the kit 100 is taken outside of a specific geographic position, also referred to as a virtual fence determined by a geolocation module).

In some embodiments, the compartment will be illuminated to show the user which compartment should be used. The tablet 114 may automatically illuminate the next compartment when it determines that the medical apparatus has made its measurement to help the patient continue in the proper sequence of operation.

Figure 4:
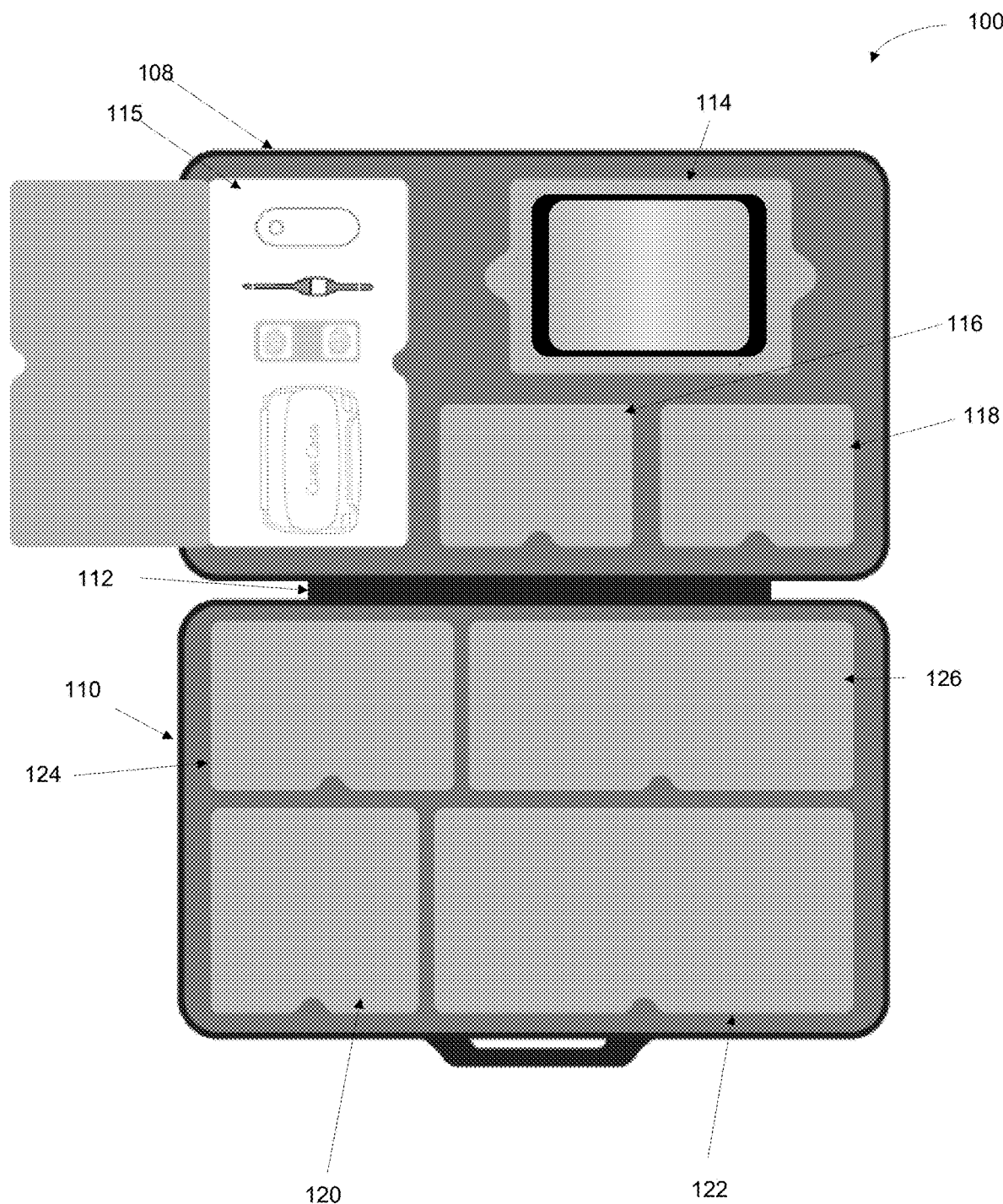
FIG. 4 shows an open portable kit with an open compartment having several physiological measuring devices in accordance with an embodiment of the present disclosure.

FIG. 4 shows an open portable kit 100 with an open compartment 115 having several physiological measuring devices in accordance with an embodiment of the present disclosure. Shown in the compartment 115 are a pulse oximeter, a thermometer, an EKG, and a blood pressure cuff.

Figure 5:
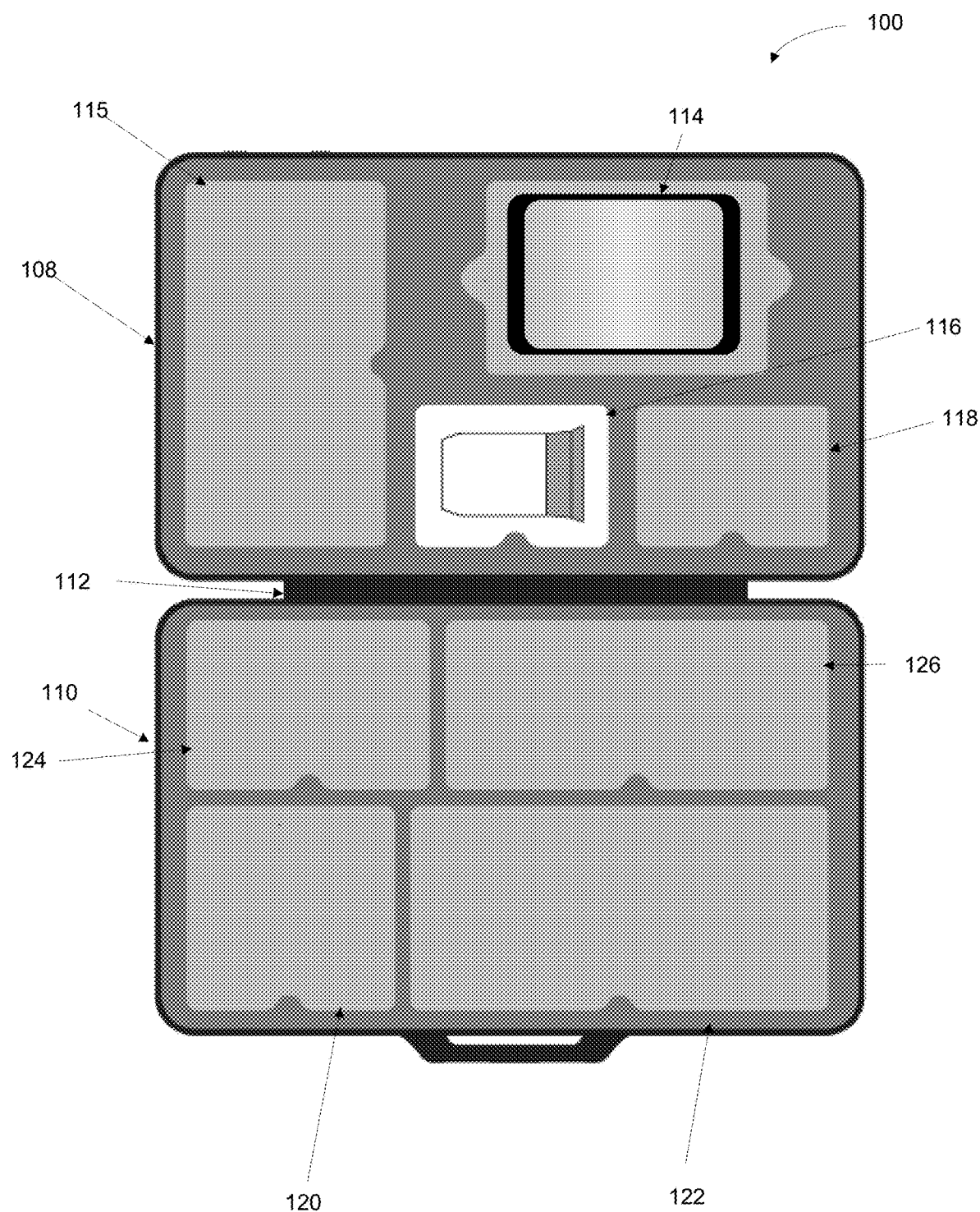
FIG. 5 shows an open portable kit with an open compartment having a pill dispenser in accordance with an embodiment of the present disclosure.

FIG. 5 shows an open portable kit 100 to a compartment 116 having a pill dispenser in accordance with an embodiment of the present disclosure. A physician may dispense a prescription that is received by the tablet 114 which in turn allows the pill dispenser to dispense a pill. The oral medicine dispensing device may be inserted into the kit 100 by a pharmacy where appropriately limited quantities of prescribed medications are included therewithin. The dispensing rules of the oral medicine dispensing device 116 can be set (and changed) by a clinician through the central control unit remotely (e.g., the tablet 114).

Figure 6:
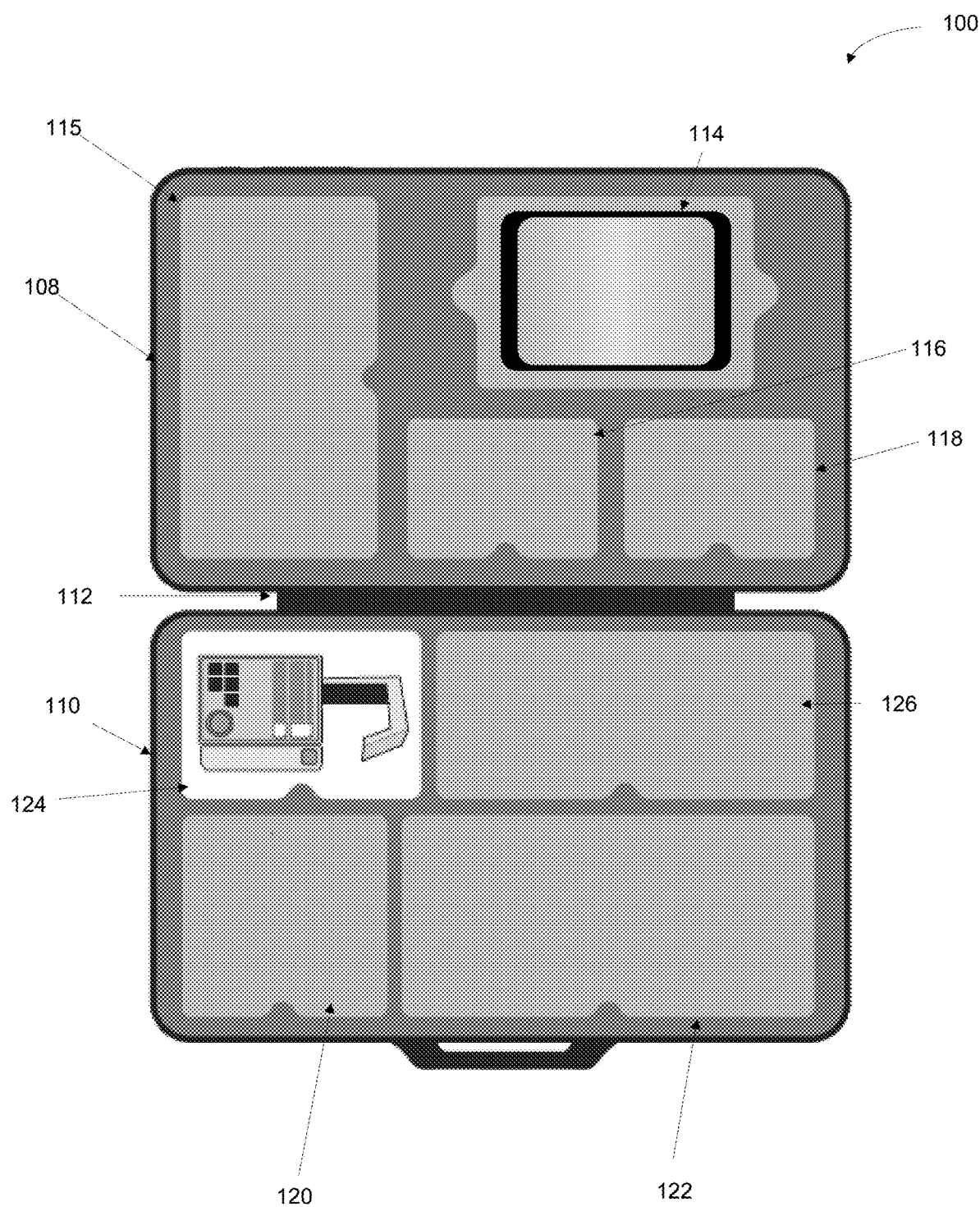
FIG. 6 shows an open portable kit with an open compartment having a gravity-based intravenous infusion pump in accordance with an embodiment of the present disclosure.

FIG. 6 shows an open portable kit 100 to a compartment having a mobile infusion pump (e.g., a gravity-based intravenous infusion pump) in the compartment 124. The mobile infusion device allows the patient or home caregiver to administer appropriate fluids (e.g. antibiotics) intravenously.

Figure 7:
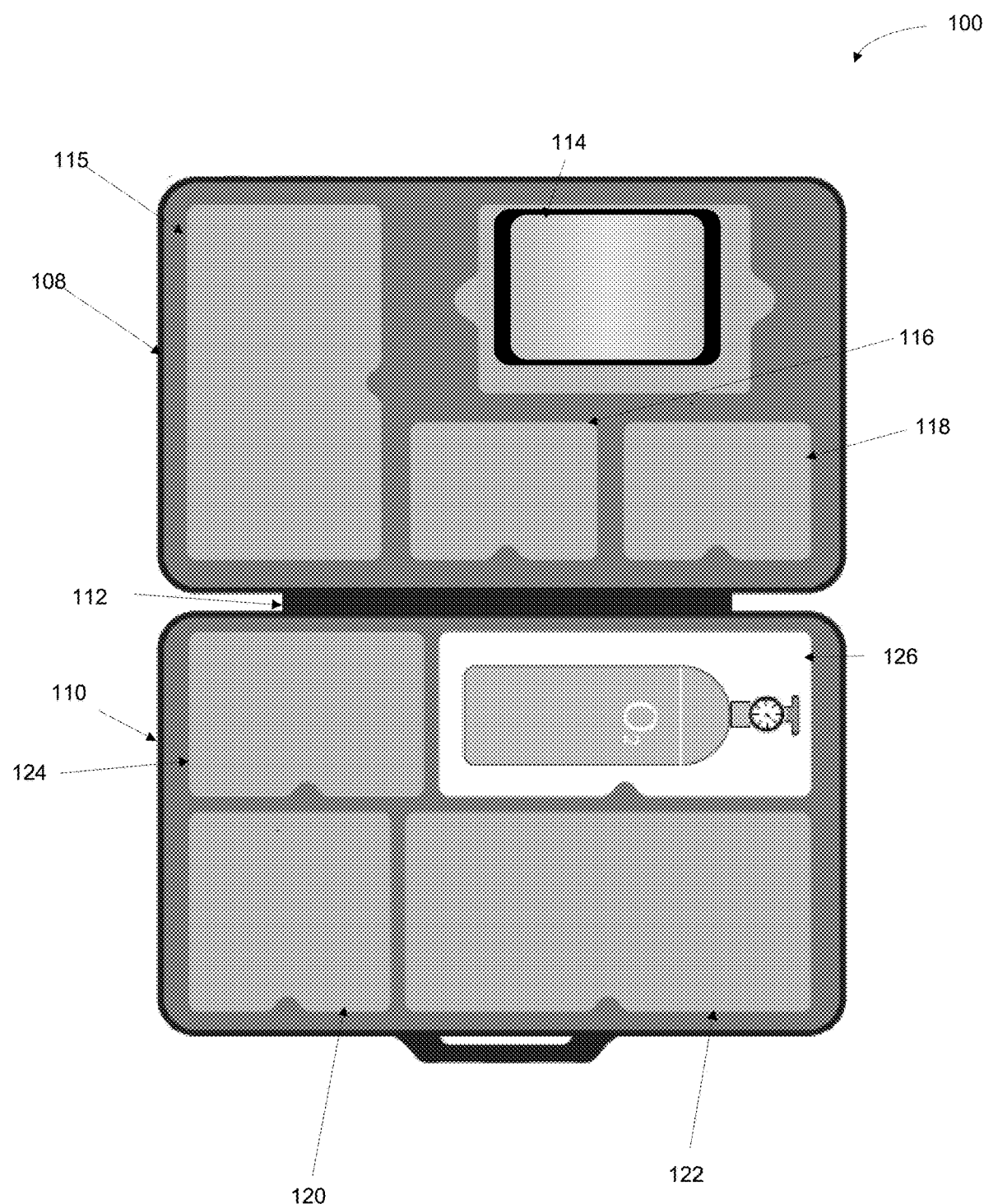
FIG. 7 shows an open portable kit with an open compartment having an oxygen tank in accordance with an embodiment of the present disclosure.
Figure 8:
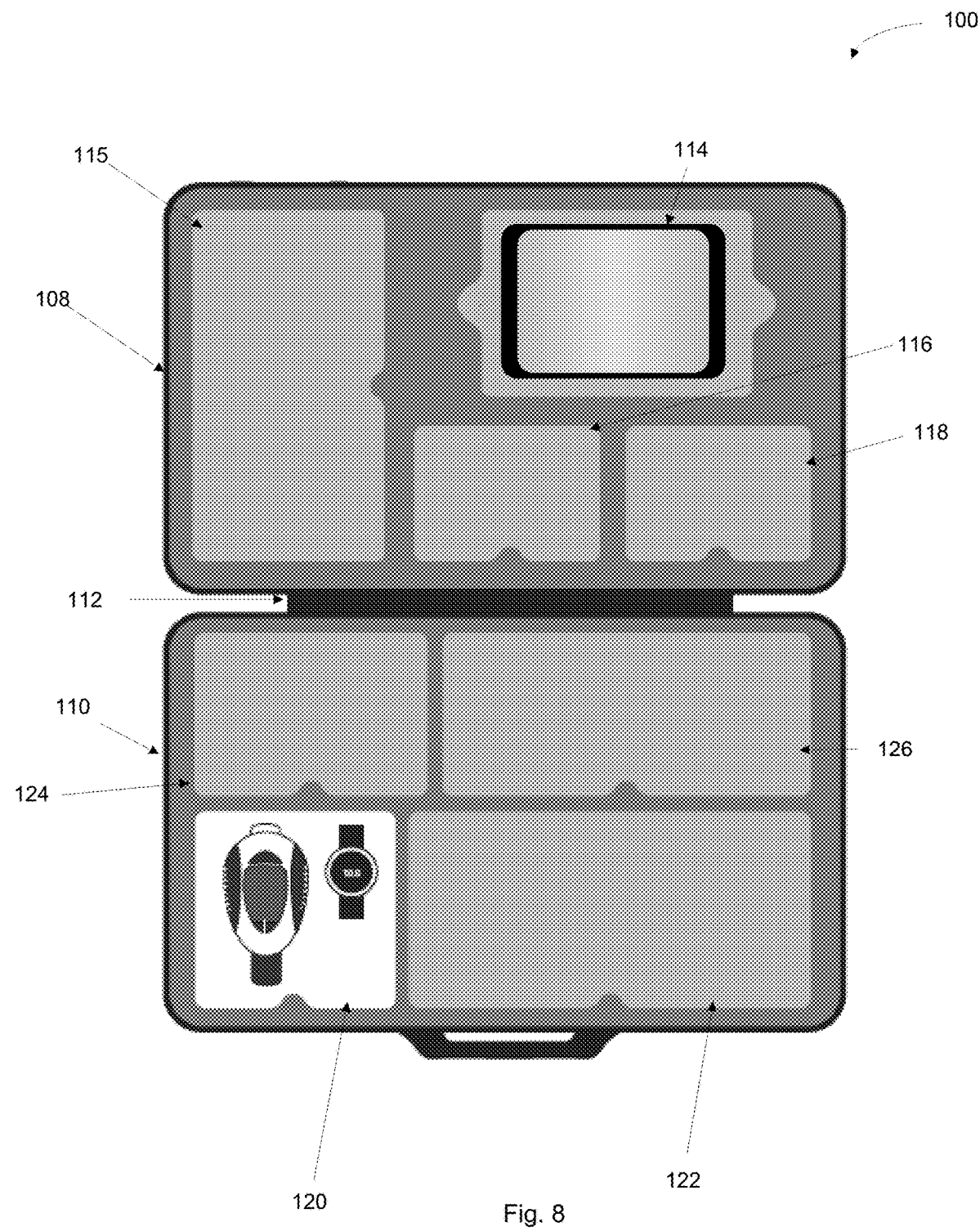
FIG. 8 shows an open portable kit with an open compartment having an activity monitor and a spirometer in accordance with an embodiment of the present disclosure.

FIG. 7 shows an open portable kit 100 to the compartment 126 having an oxygen tank. FIG. 8 shows an open portable kit 100 to a compartment 120 having an activity monitor and a spirometer in accordance with an embodiment of the present disclosure.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g., "a," "an," or "the," this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A portable patient-care kit, comprising:
   a housing including a plurality of compartments including:
      a first compartment configured to retain a first medical device; and
      a second compartment configured to receive a second medical device;
   a plurality of indicators including:
      a first indicator associated with the first compartment, the first indicator being a first illumination of the first compartment; and
      a second indicator associated with the second compartment, the second indicator being a second illumination of the second compartment; and
      a light bar disposed along an exterior of the housing, each of the first illumination, the second illumination, and the light bar being configured to indicate a communicable status, the communicable status including a use of at least one of the first medical device and the second medical device;
   a first RFID tag associated with the first medical device disposed within the first compartment, the first RFID tag providing an identification of the first medical device;
   a second RFID tag associated with the second medical device disposed within the second compartment, the second compartment providing an identification of the second medical device;
   a control unit configured to cause the first illumination and the second illumination in a sequence of operation to indicate which of the first and second compartments should be used, wherein a next one of the first and second compartments is illuminated upon a determination that one of the first and second medical devices has already made its measurement; and
   an RFID reader configured to locate the first RFID tag and the second RFID tag to determine in which of the first and second compartments the first and second medical devices are located.

2. The portable patient-care kit of claim 1, wherein the sequence of operation is configured to be provided via a remote communication from a telemedicine caregiver.

3. The portable patient-care kit of claim 1, wherein the communicable status is a prompt to perform a caregiving activity.

4. The portable patient-care kit of claim 1, wherein the plurality of indicators communicate a status with at least one of a pattern of color and intensity of at least one of the.

5. The portable patient-care kit of claim 1, wherein each of the plurality of compartments automatically open according to the sequence of operation.

6. The portable patient-care kit of claim 1, further comprising:
   a communications component configured to determine a status of at least one of the first and second medical devices.

7. The portable patient-care kit of claim 1, further comprising a battery and a power supply configured to supply power to at least one of the first and second medical devices.

8. The portable patient-care kit of claim 1, further comprising a touch-screen user interface that is pre-paired with at least one of the first and second medical devices.

9. The portable patient-care kit of claim 8, wherein the touch-screen user interface is a tablet computer.

10. The portable patient-care kit of claim 9, further comprising a communications component.

11. The portable patient-care kit of claim 10, wherein the communications component is configured to communicate with a cloud server.

12. The portable patient-care kit of claim 11, wherein the touch-screen user interface communicates with at least one of the first and second medical devices and at least one of sends and receives data with the cloud server.

13. The portable patient-care kit of claim 10, further comprising an RFID reader, wherein each of the plurality of compartments includes an RFID tag such that the RFID reader is configured to determine in which of the plurality of compartments a readable tag associated with at least one of the first and second medical devices is disposed.

14. The portable patient-care kit of claim 13, wherein data is configured to be communicated from the RFID tag to the RFID reader, and further comprising an alarm that alerts upon the data communicated from the RFID tag to the RFID reader satisfies a condition.

15. The portable patient-care kit of claim 1, further comprising an environmental monitor component disposed within the housing.

16. The portable patient-care kit of claim 15, wherein the environmental monitor component monitors a measured parameter and communicates the measured parameter to a cloud server.

17. The portable patient-care kit of claim 16, wherein the measured parameter is at least one of temperature, humidity, location, vibration, shocks, and atmospheric pressure.

* * * * *